(12) United States Patent
Iwema Bakker et al.

(10) Patent No.: US 7,244,734 B2
(45) Date of Patent: Jul. 17, 2007

(54) HEXA- AND OCTAHYDRO-PYRIDO[1,2-A]PYRAZINE DERIVATIVES WITH NK₁ ANTAGONISTIC ACTIVITY

(75) Inventors: Wouter I. Iwema Bakker, Weesp (NL); Gustaaf J. M. Van Scharrenburg, Weesp (NL); Adrianus Van Den Hoogenband, Weesp (NL); Andrew C. McCreary, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 314 days.

(21) Appl. No.: 10/946,176

(22) Filed: Sep. 22, 2004

(65) Prior Publication Data

US 2005/0070548 A1    Mar. 31, 2005

Related U.S. Application Data

(60) Provisional application No. 60/505,873, filed on Sep. 26, 2003.

(51) Int. Cl.
*A01N 43/58*     (2006.01)
*A01N 43/60*     (2006.01)
*A61K 31/50*     (2006.01)
*A61K 31/495*    (2006.01)
*C07D 401/00*    (2006.01)

(52) U.S. Cl. .................. 514/249; 544/333; 544/335; 544/349

(58) Field of Classification Search ............ None
See application file for complete search history.

(56) References Cited

U.S. PATENT DOCUMENTS 6,284,757 B1 *  9/2001  Sanner .................. 514/249

FOREIGN PATENT DOCUMENTS

EP      0 655 442 A       5/1995
GB      1125112      *    8/1968
WO      WO 03/084955      10/2003

OTHER PUBLICATIONS

Al-Dabbagh and Smith, "Species differences in oxidative drug metabolism: some basic considerations." Archives of toxicology. Supplement. Archiv fur Toxikologie. supplement, vol. 7, pp. 219-231 (1984).*
Hans Bundgaard, Design of Prodrugs, p. 1. © 1985 Elsevier Science Publishers.*
Richard B. Silverman, The Organic Chemistry of Drug Design and Drug Action, pp. 352-400. © 1992 Academic Press, Inc.*
Humphrey, J.M. "Medicinal Chemistry of Selective Neurokinin-1 Antagonists" Current Topics in Medicinal Chemistry, vol. 3(12), pp. 1423-1435 (2003).*

* cited by examiner

*Primary Examiner*—Zachary C Tucker
(74) *Attorney, Agent, or Firm*—Finnegan, Henderson, Farabow, Garrett & Dunner, L.L.P.

(57) ABSTRACT

The invention relates to hexahydro-pyrido[1,2-a]pyrazine derivatives having interesting neurokinin-NK₁ receptor antagonistic activity. The invention also relates to methods for the preparation of these compounds, to pharmaceutical compositions containing a pharmacologically active amount of at least one of these compounds as an active ingredient, as well as to the use of these compositions for the treatment of disorders in which neurokinin receptors are involved. The invention relates to compounds represented by the general formula (1)

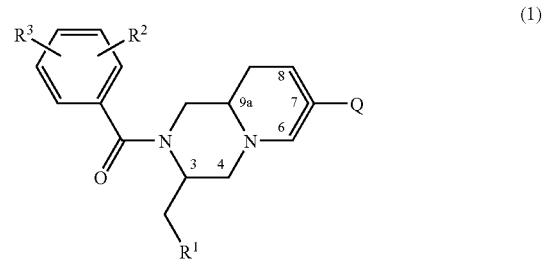

(1)

wherein the symbols have the meanings as given in the description.

8 Claims, No Drawings

HEXA- AND OCTAHYDRO-PYRIDO[1,2-A]PYRAZINE DERIVATIVES WITH NK₁ ANTAGONISTIC ACTIVITY

CROSS REFERENCE TO RELATED APPLICATIONS

This application claims the benefit of U.S. Provisional Application No. 60/505,873, filed Sep. 26, 2003, and claims the right to priority based on European Application No. 03103566.0, filed Sep. 26, 2003 the content of both of which is incorporated herein by reference The present invention relates to hexa- and octahydro-pyrido[1,2-a]pyrazine derivatives having interesting neurokinin-$NK_1$ receptor antagonistic activity. The invention also relates to methods for the preparation of these compounds, to pharmaceutical compositions containing a pharmacologically active amount of at least one of these compounds as an active ingredient, as well as to the use of these compositions for the treatment of disorders in which neurokinin receptors are involved.

From the European patent application EP 0655442 piperazine derivatives with neurokinin antagonistic activity are known. Piperazine derivatives sharing this biological activity were also disclosed in EP 0899270 which describes a series of 2-(3-indolylmethyl)-1-benzoyl-4-[(2-(benzylamino)ethyl)aminocarbonyl)] piperazine derivatives having $NK_1$ antagonistic activity.

Surprisingly, it has now been found that piperazine derivatives are also $NK_1$ antagonists when the piperazine ring and it's N-4 substituent are fused to yield hexa- or octahydro-pyrido[1,2-a]pyrazine derivatives.

The invention relates to compounds of the general formula (1)

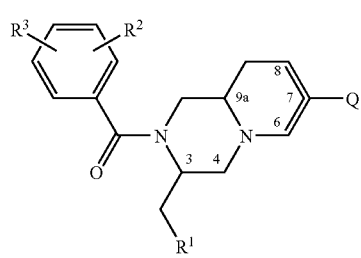

wherein:
$R^1$ represents phenyl, 2-indolyl, 3-indolyl, 3-indazolyl or benzo[b]thiophen-3-yl, which groups may be substituted with halogen or alkyl (1-3C), $R^2$ and $R^3$ independently represent halogen, H, $OCH_3$, $CH_3$ and $CF_3$, Q represents an optionally substituted aromatic or heteroaromatic five- or six-membered ring, connected by a carbon-carbon bond, the pyrido[1,2-a]pyrazine moiety may or may not contain a double bond between either carbon atoms 6 and 7 or between carbon atoms 7 and 8, and pharmacologically acceptable salts and prodrugs thereof.

All compounds having formula (1) in which the asymmetrical carbon atoms 3 and 9a, as well as the potentially asymmetrical carbon atom 7, are in either the R-configuration or the S-configuration belong to the invention.

Also prodrugs, i.e. compounds which when administered to humans by any known route, are metabolised to compounds having formula (1), belong to the invention. In particular this relates to compounds with primary or secondary amino or hydroxy groups. Such compounds can be reacted with organic acids to yield compounds having formula (1) wherein an additional group is present which is easily removed after administration, for instance, but not limited to amidine, enamine, a Mannich base, a hydroxylmethylene derivative, an O-(acyloxymethylene carbamate) derivative, carbamate, ester, amide or enaminone. A prodrug is an inactive compound, which when absorbed is converted into an active form (Medicinal Chemistry: Principles and Practice, 1994, ISBN 0-85186-494-5, Ed.: F. D. King, p. 216).

Suitable acid addition salts can be formed with inorganic acids or with organic acids.

The invention particularly relates to compounds having formula (1) in which Q is an optionally substituted six-membered nitrogen containing heteroaromatic ring, and in which the other symbols have the meanings as given above, and including all possible stereo-isomers as outlined above.

Even more preferred are compounds having formula (1) wherein $R^1$ is 3-indolyl, $R^2$ and $R^3$ are $CF_3$ groups in the 3- and 5-positions, and Q is an optionally substituted six-membered nitrogen containing heteroaromatic ring, and including all possible stereo-isomers as outlined above.

In the description of the substituents the abbreviation 'alkyl(1-3C)' means 'methyl, ethyl, n-propyl or isopropyl'. In this specification, 'optionally substituted' means that a group may or may not be further substituted by one or more groups selected from alkyl, alkenyl, alkynyl, aryl, fluoro, chloro, bromo, hydroxyl, alkyloxy, alkenyloxy, aryloxy, acyloxy, amino, alkylamino, dialkylamino, arylamino, thio, alkylthio, arylthio, cyano, oxo, nitro, acyl, amido, alkylamido, dialkylamido, carboxyl, or two optional substituents may together with the carbon atoms to which they are attached form a 5- or 6-membered aromatic or non-aromatic ring containing 0, 1 or 2 heteroatoms selected from nitrogen, oxygen or sulphur. 'Heteroaromatic' means containing at least one N, O or S atom. 'Five- or six-membered rings' are for example: furan, thiophene, pyrrole, oxazole, thiazole, imidazole, pyrazole, isoxazole, isothiazole, 1,2,3-oxadiazole, 1,2,3,-triazole, 1,3,4-thiadiazole, pyridine, pyridazine, pyrimidine or pyrazine rings.

The compounds of the invention of the general formula (1), as well as the salts thereof, have $NK_1$ antagonistic activity and show a good bioavailability. They are useful in the treatment of disorders in which neurokinins which interact with $NK_1$ receptors, e.g. neurokinin-1 (=Substance P) are involved, or that can be treated via manipulation of those systems. For instance in acute and chronic pain, emesis, inflammatory diseases such as meningitis, arthritis, asthma, psoriasis and (sun)burns; gastro-intestinal disorders, in particular irritable bowel syndrome, inflammatory bowel disease (Crohn's disease), ulcerative colitis; bladder or GI tract hypermotility disorders, urinary tract inflammation; allergic responses such as eczema and rhinitis; cardio-vascular disorders such as hypertension, atherosclerosis, edema, angina, cluster headache and migraine; cutaneous diseases such as urticaria, lupus erythematosus and pruritus; respiratory disorders including chronic obstructive pulmonary disease, bronchospams, bronchopneumonia, bronchitis, respiratory distress syndrome and cystic fibrosis; various neoplastic diseases; psychiatric and/or neurological disorders such as schizophrenia and other psychotic disorders; mood disorders such as bipolar I disorders, bipolar II disorders and unipolar depressive disorders like minor depression, seasonal affective disorder, postnatal depression dysthymia and major depression; anxiety disorders including panic disorder (with or without agoraphobia), social phobia, obsessive compulsive disorder (with or without co-morbid chronic tic or schizotypal disorder), posttraumatic stress disorder and generalized anxiety disorder; substance related disorders, including substance use disorders (like dependence and abuse) and substance induced disorders (like substance withdrawal); pervasive development disorders including autistic disorder and Rett's disorder; attention deficit and disruptive behavior disorders such as attention deficit hyperactivity disorder; impulse control disorders like agression, pathological gambling; eating disorders like anorexia nervosa and bulimia nervosa, obesity; sleep disorders like insomnia; tic disorders like Tourette's disorder; restless legs syndrome; disorders characterized by impairment of cognition and memory such as Alzheimer's disease, Creutzfeldt-Jacob disease, Huntington's disease, Parkinson's disease and neurorehabilitation (post-traumatic brain lesions)

The NK1 antagonistic properties of the compounds of the invention were tested using the methods outlined below.

Pharmacological Methods

Receptor Binding for Human $NK_1$ Receptors

Affinity of the compounds for human $NK_1$ receptors was assessed using radio-receptor binding assays. Membrane preparations were prepared from Chinese Hamster Ovarium fibroblast (CHO) cells in which the human $NK_1$ receptor was stably expressed. Membranes were incubated with [$^3$H]-substance P in the absence or the presence of specified concentrations of the compounds, diluted in a suitable buffer in presence of peptidase inhibitor for 10 min at 25° C. Separation of bound radioactivity from free was done by filtration over Whatman GF/B glass fiber filters with two 5 sec washings. Bound radioactivity was counted by liquid scintillation counting using a Betaplate counter. Measured radioactivity was plotted against the concentration of the displacing test compound and displacement curves were calculated by four-parameter logistic regression, resulting in $IC_{50}$ values, i.e. that concentration of displacing compound by which 50% of the radioligand is displaced. Affinity $pK_I$ values were calculated by correcting the $IC_{50}$ values for radioligand concentration and its affinity for the human $NK_1$ receptor according to the Cheng-Prusoff equation:

$$pK_i = -\log [IC_{50}/(1+S/K_d)]$$

in which the $IC_{50}$ is as described above, S is the concentration [$^3$H]-substance P used in the assay expressed in mol/l, and $K_d$ is the equilibrium dissociation constant of [$^3$H]-substance P for human $NK_1$ receptors (in mol/l).

cAMP Measurements

The effects of test compounds at formation of cyclic AMP (cAMP) was assessed using CHO fibroblast cells, stably expressing cloned human $NK_1$ receptors. In addition to coupling to phospholipase C, human $NK_1$ receptors are also able to stimulate adenylate cyclase, which converts ATP into cAMP. For tests, cells were cultured in 24-well plates. Prior to experiments, medium was replaced by serum-free α-DMEM culture medium, containing [$^3$H]-adenine which is taken up by the cells and converted sequentially into radiolabeled adenosine, AMP, ADP and ultimately into radiolabeled ATP. After 2 hrs, cells were rinsed twice with phosphate-buffered saline (pH 7.4) in presence of 1 mM isobutylmethylxanthine (IBMX; inhibitor of phosphodiesterases that hydrolyse cAMP into AMP). Subsequently, cells were stimulated by 10 nM substance P in absence or presence of test compounds in appropriate dilutions in PBS/IBMX for 20 min. After stimulation, medium was aspirated and cells were extracted by 5% trichloroacetic acid. Radiolabeled ATP and cAMP were recovered from the extracts using sequential column chromatography. Extracts were separated by ion-exchange chromatography over DOWEX 50WX4 columns, allowing the recovery of ATP. Columns were subsequently put on top of aluminum oxide columns and eluted with water. Recovery of cAMP was performed by eluting the aluminum oxide columns with 100 mM imidazole (pH 7.4). Both ATP and cAMP fractions were counted for radioactivity using liquid scintillation counting and conversion ratios were calculated as:

$$v = [cAMP] * 100\% / ([ATP] + [cAMP]).$$

Concentration-response relationships were constructed by plotting cAMP conversion against compound concentration and $IC_{50}$ values were calculated by four-parameter logistic regression. Antagonist potencies ($pA_2$) values were calculated using:

$$pA_2 = IC_{50}/(1+[SP]/EC_{50})$$

in which the $IC_{50}$ of the test compound was obtained from concentration-effect relationships, [SP] is the concentration of substance P (in mol/l; typically 10 nM), and the $EC_{50}$ is the potency of substance P at human cloned $NK_1$ receptors.

$NK_1$ Agonist—Induced Gerbil Foot-Tapping

The ability of NK1 antagonists to antagonise foot-tapping induced by centrally administered $NK_1$ agonists has been demonstrated (Rupniak and Williams, 1994 (Eur. J. Pharmacol. 265:179); Bristow and Young, 1994 (Eur. J. Pharmacol. 253: 245)). Therefore, we have used this model to assess the in vivo activity of the compounds of the invention.

60 min prior to anaesthesia with $N_2O$ (0.8 L/min), halothane (3%) and $O_2$ (0.8 L/min) male gerbils (40-60 g; Charles River) received an injection of vehicle or test compound (p.o.). Upon successful narcosis the anaesthetic was adjusted to $N_2O$ (0.6 L/min), halothane (1.5%) and $O_2$ (0.6 L/min) and a midline scalp incision made. GR 73632 was infused into the cerebroventricular space (AP−0.5 mm, L−1.2 mm, and vertical−4.5 mm from bregma). Following recovery from anaesthesia (about 3-4 min) the foot tapping response was recorded for 5 minutes. The predefined criterion for antagonism of this response was defined as inhibition of foot tapping for ≧5 min.

The compounds of the invention, as exemplified by the compounds 1-6, have a high affinity for NK1 receptors with $pK_i$-values≧7.0 in the binding assay described above. As outlined in detail in the examples given, some of these compounds have been used as intermediates in the synthesis of other compounds. The compounds of the invention are active in the cAMP assay, their $pA_2$-values being in line with their $pK_i$-values. Some of the compounds belonging to the invention penetrate the blood brain barrier as is evident from their activity in the neurokinin-agonist induced gerbil foot tapping assay. This property makes them useful in the treatment of CNS disorders.

The compounds having formula (1) and their salts can be obtained according to at least one of the following methods known for compounds of this type.

The compounds of the present invention may be prepared by the general route outlined in Scheme 1. Thus reaction of an amino acid ester with 5-oxo-piperidine-1,2-dicarboxylic acid 1-benzyl ester (H. C. Beyerman, P. Boekee *Recl. Trav. Chim. Pays-Bas,* 1959, 78, 648) under standard peptide coupling procedures as described in M. Bodanszky, A. Bodanszky *The Practice of Peptide Synthesis*, Springer-Verlag, 1994; ISBN: 0-387-57505-7 afforded dipeptides I, use of a chiral amino acid would result in the formation of diastereomers and these can be separated at this (or a later) stage using standard chromatographic methods. Protection of the ketone in I as a cyclic or acyclic ketal, such as those described in T. W. Greene, P. G. M. Wuts *Protective Groups in Organic Synthesis*, John Wiley & Sons, 1999, yields compounds of formula

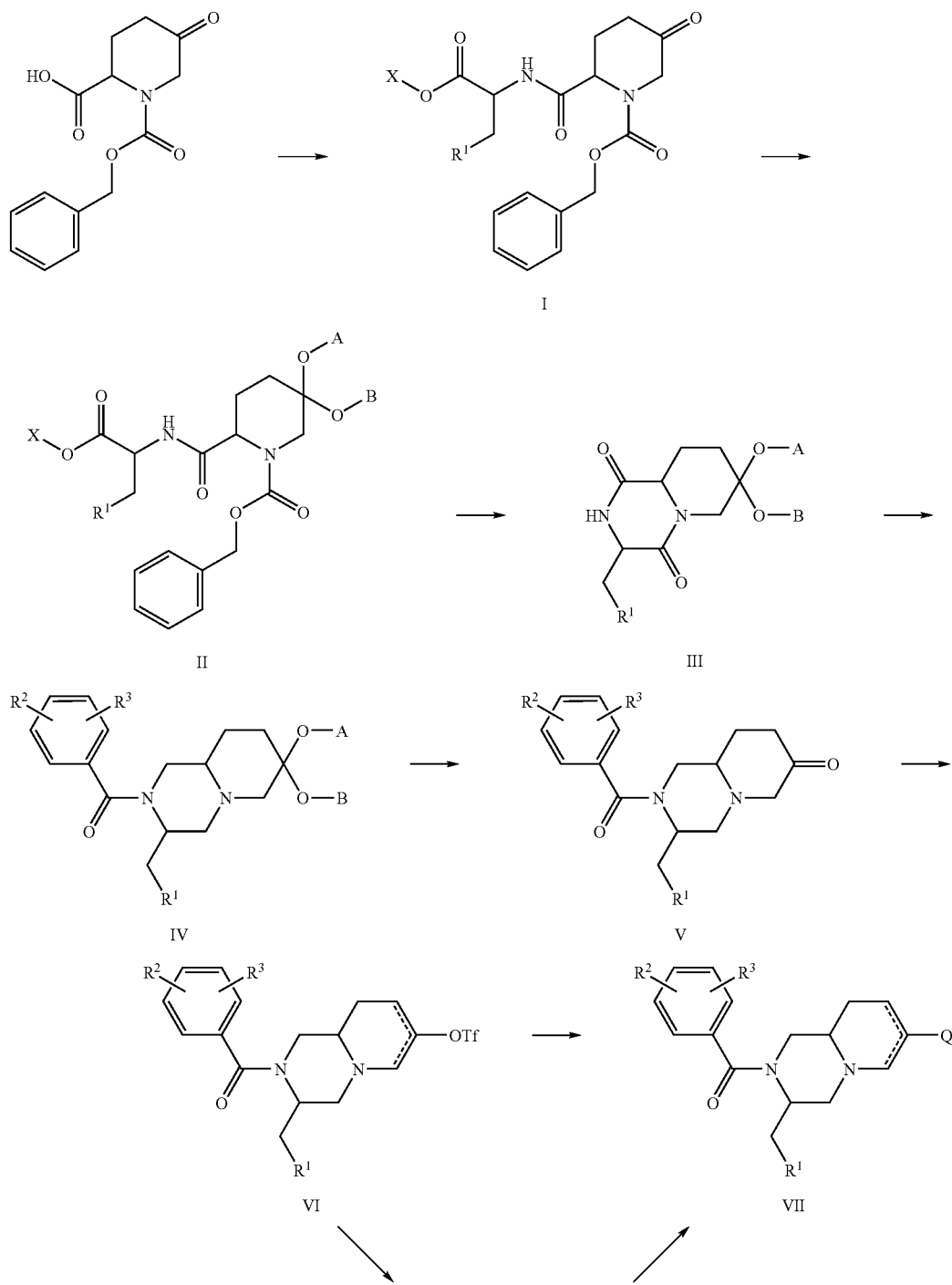

Scheme 1

-continued

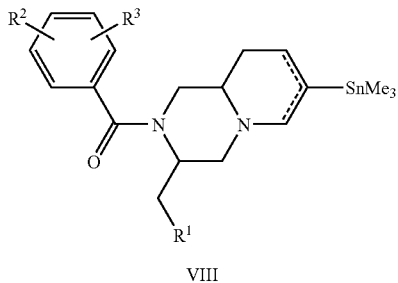

VIII

II, in which A and B represent a cyclic or acyclic ketal. This reaction can be conducted following conventional methods that are generally known in the art. Removal of the benzyloxycarbonyl group under reductive conditions (H$_2$, Pd/C) in a solvent such as methanol, followed by acid catalyzed cyclisation afforded diketopiperazines of formula III. Reduction of III with an active hydride reagent such as lithium aluminum hydride leads to an amine, which can be acylated with an appropriate acid chloride, under conditions that are generally known in the art, to afford IV. Hydrolysis of the ketal to form V can be done by methods as described in T. W. Greene, P. G. M. Wuts *Protective Groups in Organic Synthesis*, John Wiley & Sons, 1999. In cases were R$^1$ contains an NH-group, as for example in an indolyl- or indazolyl-group, the NH is protected with a tert-butyloxycarbonyl group done by methods as described in T. W. Greene, P. G. M. Wuts *Protective Groups in Organic Synthesis*, John Wiley & Sons, 1999. After eventual protection of R$^1$, compound V is converted to triflate VI by treatment with a lithium-amide base, such as lithium bis(trimethylsilyl)amide, in an ethereal solvent, such as tetrahydrofuran, at low temperature (−70° C.), followed by the addition of a bis(trifluoromethanesulfonimide), such as N-phenyl-bis(trifluoromethanesulfonimide). Triflate VI can be coupled, under palladium catalysis, with an aromatic or heteroaromatic stannane in a solvent such as 1,4-dioxane, to afford the compounds of the present invention VII. In an alternative route triflate VI is converted to stannane VIII with hexamethylditin, under palladium catalysis, in a solvent such as tetrahydrofuran; subsequently stannane VIII can be coupled with an appropriate aromatic or heteroaromatic halide, under palladium catalysis, in a solvent such as N,N-dimethylformamide to afford compounds VII.

The compounds VI and VIII were isolated as mixtures of double bond isomers or as a single isomer for which the position of the double bond was not determined. Compounds VII were initially formed as mixtures of double bond isomers, which could be isomerised to the most stable configuration in which the double bond is in between the carbonatoms 6 and 7.

Details of compounds synthesized by this route are given in the examples below.

SPECIFIC EXAMPLES OF SYNTHESES

Example 1 (See Scheme 1)

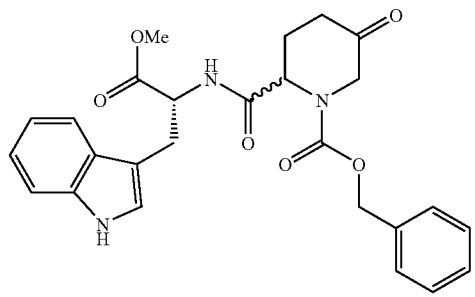

To a solution of 5-oxo-piperidine-1,2-dicarboxylic acid 1-benzyl ester (93.5 g) in acetonitrile (1 L) was added a solution of diisopropylcarbodiimide (53 ml) in acetonitrile (50 ml) and the mixture was cooled to 5° C. To the resulting suspension was added portion-wise D-tryptophan methyl ester hydrochloride (85.5 g) and drop-wise a solution of diisopropylethylamine (58.6 ml) in acetonitrile (50 ml). The resulting mixture was stirred 18 hours at room temperature then filtered and concentrated in vacuo. The residue was dissolved in dichloromethane washed with hydrochloric acid (1 M) twice and water twice, dried, filtered and concentrated in vacuo to afford a mixture of (2R,2'R)- and (2S,2'R)-2-[2-(1H-Indol-3-yl)-1-methoxycarbonyl-ethylcarbamoyl]-5-oxo-piperidine-1-carboxylic acid benzyl ester (171.2 g) which was used as such in the next step.

Example 2

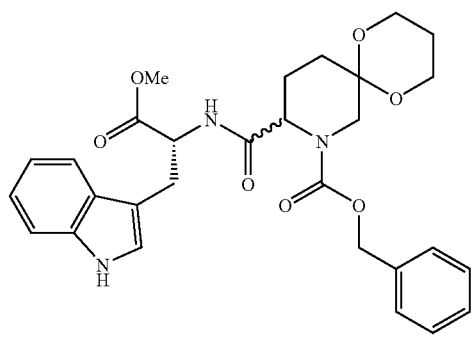

A mixture of (2R,2'R)- and (2S,2'R)-2-[2-(1H-Indol-3-yl)-1-methoxycarbonyl-ethyl-carbamoyl]-5-oxo-piperidine-1-carboxylic acid benzyl ester (138.9 g), oxalic acid (180 g) and 1,3-propanediol (87 ml) in acetonitrile (1.5 L) was heated at 40° C. for 20 hours. Subsequently the solvent was removed in vacuo and the residue purified by flash chromatography (SiO₂, CH₂Cl₂/MeOH 99:1) to afford a mixture of (9R,2'R)- and (9S,2'R)-9-[2-(1H-Indol-3-yl)-1-methoxycarbonyl-ethylcarbamoyl]-1,5-dioxa-8-aza-spiro[5.5]undecane-8-carboxylic acid benzyl ester (118 g). MH⁺ 536, $R_f$ 0.07 (SiO₂, CH₂Cl₂/MeOH 99:1).

Example 3

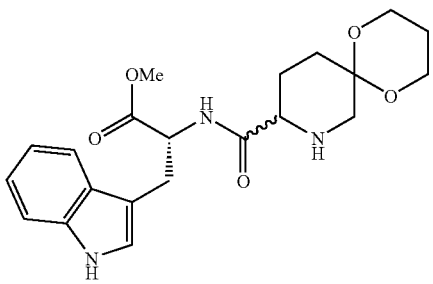

To a solution of a mixture of (9R,2'R)- and (9S,2'R) 9-[2-(1H-lndol-3-yl)-1-methoxycarbonyl-ethylcarbamoyl]-1,5-dioxa-8-aza-spiro[5.5]undecane-8-carboxylic acid benzyl ester (92.8 g) in methanol (1 L) was added 10% palladium on carbon (approximately 5 g). The resulting mixture was hydrogenated with H₂ (1 atm.) overnight at room temperature. The catalyst was removed by filtration over Celite and the remaining solution was concentrated in vacuo to afford a mixture of (2R,9'R) and (2R,9'S)-2-[(1,5-Dioxa-8-aza-spiro[5.5]undecane-9-carbonyl)-amino]-3-(1H-indol-3-yl)-propionic acid methyl ester (69.0 g). $R_f$ 0.24 (SiO₂, CH₂Cl₂/MeOH/NH₄OH 92:7.5:0.5).

Example 4

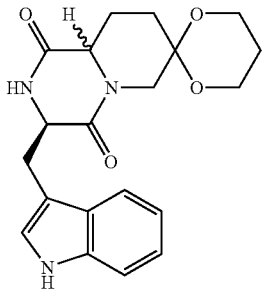

A mixture of (2R,9'R) and (2R,9'S)-2-[(1,5-Dioxa-8-aza-spiro[5.5]undecane-9-carbonyl)-amino]-3-(1H-indol-3-yl)-propionic acid methyl ester (69.0 g) and acetic acid (9 ml) in acetonitrile (900 ml) was heated under reflux overnight. After cooling to room temperature the mixture was concentrated to approximately one third its original volume. The formed precipitate was collected by filtration to afford (3R,9aS)-3-(1H-indol-3-ylmethyl)-hexahydro-spiro[2H-pyrido[1,2-a]pyrazine-1,4-dione-7,2'-[1,3]dioxane] (23.7 g; $R_f$ 0.34 (Et₂O/MeOH 9:1)). Concentration of the filtrate and purification of the residue by flash chromatography (SiO₂, Et₂O/MeOH 9:1) afforded (3R,9aR)-3-(1H-indol-3-ylmethyl)-hexahydro-spiro[2H-pyrido[1,2-a]pyrazine-1,4-dione-7,2'-[1,3]dioxane] (20.6 g; $R_f$ 0.18 (SiO₂, Et₂O/MeOH 9:1).

Example 5

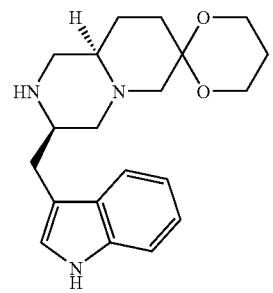

To a suspension of lithium aluminum hydride (10.6 g) in THF (500 ml) was added drop-wise a solution of (3R,9aR)-3-(1H-indol-3-ylmethyl)-hexahydro-spiro[2H-pyrido[1,2-a]pyrazine-1,4-dione-7,2'-[1,3]dioxane] (20.6 g) in THF (100 ml), and the resulting mixture was heated under reflux for 2 days. After cooling to 5° C. water (9.2 ml) 2M sodium hydroxide (aq, 18.4 ml), and again water (9.2 ml) were added drop-wise. The resulting mixture was heated under reflux for another hour, cooled to room temperature, filtered over Celite, and concentrated in vacuo to afford crude (3R,9aR)-3-(1H-indol-3-ylmethyl)-octahydro-spiro[2H-pyrido[1,2-a]pyrazine-7,2'-[1,3]dioxane] (19.7 g, $R_f$ 0.16 (SiO₂, CH₂Cl₂/MeOH/NH₄OH 92:7.5:0.5)) which was used as such in the next step.

Example 6

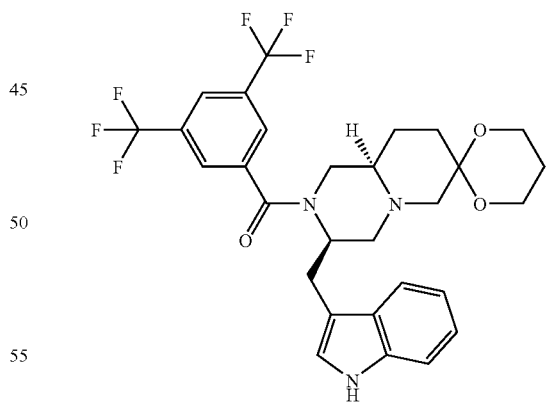

To a solution of (3R,9aR)-3-(1H-indol-3-ylmethyl)-octahydro-spiro[2H-pyrido[1,2-a]pyrazine-7,2'-[1,3]dioxane] (19.7 g) in dichloromethane was added diisopropylethylamine (9.6 ml) at room temperature and at 5° C., 3,5-bis(trifluoromethyl)benzoyl chloride (10 ml) drop-wise. The resulting mixture was stirred at room temperature overnight, concentrated in vacuo and purified by column chromatography (SiO₂, CH₂Cl₂/MeOH/NH₄OH 96:3.75:0.25) to afford (3R,9aR)-2-[3,5-bis(trifluoromethyl)benzoyl]-3-(1H- indol-3-ylmethyl)-octahydro-spiro-[2H-pyrido-[1,2-a]pyrazine-7,2'-[1,3]dioxane] (30.0 g). R$_f$ 0.35 (SiO$_2$, CH$_2$Cl$_2$/MeOH/NH$_4$OH 96:3.75:0.25).

Example 7

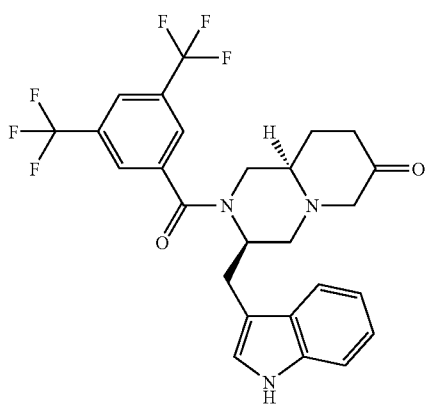

A mixture of (3R,9aR)-2-[3,5-bis(trifluoromethyl)benzoyl]-3-(1H-indol-3-ylmethyl)-octahydro-spiro-[2H-pyrido[1,2-a]pyrazine-7,2'-[1,3]dioxane] (30.0 g) in acetic acid (150 ml) and 6M hydrochloric acid (150 ml) was heated at 40° C. for three days. After cooling to room temperature dichloromethane (750 ml) and 2M sodium hydroxide (aq., 1700 ml) were added. The layers were separated and the aqueous layer was extracted twice with dichloromethane. The combined organic layers were washed with water, concentrated in vacuo, and purified by flash-chromatography (SiO$_2$, CH$_2$Cl$_2$/MeOH 98:2) to afford (3R,9aR)-2-[3,5-bis(trifluoromethyl)benzoyl]-3-(1H-indol-3-ylmethyl)-octahydro-2H-pyrido[1,2-a]pyrazin-7-one (21.7 g). R$_f$ 0.12 (SiO$_2$, CH$_2$Cl$_2$/MeOH 98:2).

Example 8

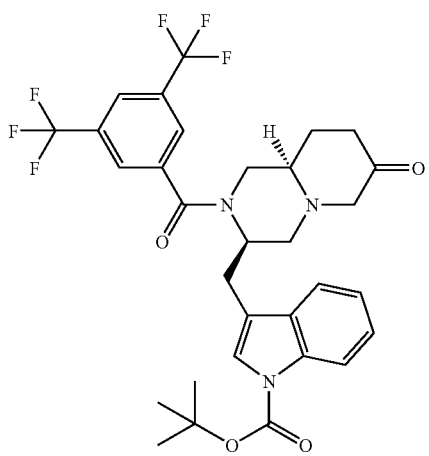

To a suspension of (3R,9aR)-2-[3,5-bis(trifluoromethyl)benzoyl]-3-(1H-indol-3-ylmethyl)-octahydro-2H-pyrido[1,2-a]pyrazin-7-one (12.0 g), triethylamine (2.93 g), and 4-dimethylaminopyridine (600 mg) in acetonitrile (125 ml) was added drop wise a solution of di-tert-butyl dicarbonate (6.4 g) in acetonitrile (50 ml), at room temperature. The resulting mixture was stirred at room temperature for 2.5 h, and concentrated in vacuo. The residue was dissolved in dichloromethane washed with aqueous sodium bicarbonate (5%), dried, filtered and concentrated in vacuo, and purified by flash-chromatography (SiO$_2$, CH$_2$Cl$_2$/MeOH 98.5:1.5) to afford (3R,9aR)-3-[2-(3,5-bis(trifluoromethyl)benzoyl)-7-oxo-octahydro-pyrido[1,2-a]pyrazin-3-ylmethyl]-indole-1-carboxylic acid tert-butyl ester (11 g). R$_f$ 0.46 (SiO$_2$, CH$_2$Cl$_2$/MeOH 95:5).

Example 9

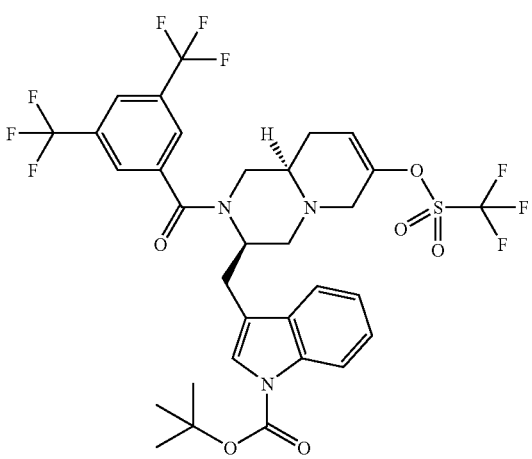

and

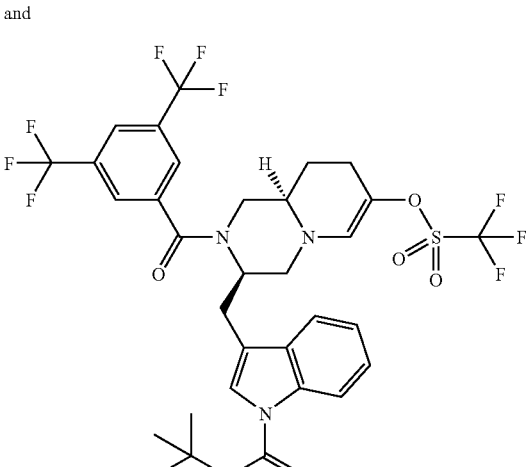

To a solution of lithium bis(trimethylsilyl)amide (1.0 g) in tetrahydrofuran (35 ml) was added drop wise a solution of (3R,9aR)-3-[2-(3,5-bis(trifluoromethyl)benzoyl)-7-oxo-octahydro-pyrido[1,2-a]pyrazin-3-ylmethyl]-indole-1-carboxylic acid tert-butyl ester (2.8 g) in tetrahydrofuran (30 ml), at −70° C. After stirring, at −70° C., for 1.5 h a solution of N-phenyl-bis(trifluoromethanesulfonimide) (2.15 g) in tetrahydrofuran (10 ml) was added drop wise. After the addition was complete the solution was allowed to come to room temperature overnight, then quenched with methanol (5 ml), concentrated in vacuo and purified by column chromatography (SiO$_2$, CH$_2$Cl$_2$/MeOH 99:1) to afford a mixture of (3R,9aR)-3-[2-(3,5-bis(trifluoromethyl)benzoyl)-7-trifluoromethanesulfonyloxy-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis (trifluoromethyl)-benzoyl)-7-trifluoromethanesulfonyloxy-1,3,4,8,9,9a-hexahydro-2H-pyrido[1,2-a]pyrazin-3-ylmethyl]-indole-1-carboxylic acid tert-butyl ester (3.4 g). $R_f$ 0.75 (SiO$_2$, CH$_2$Cl$_2$/MeOH 99:1).

Example 10

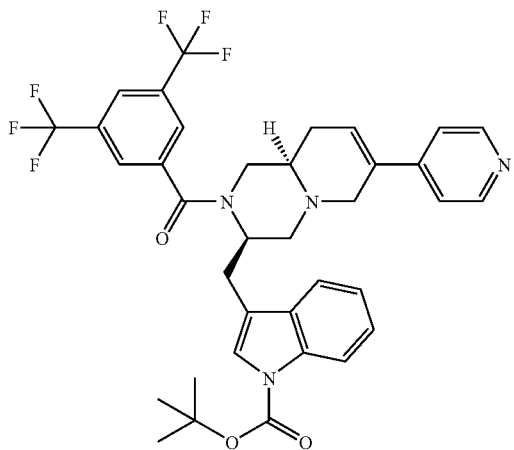

and

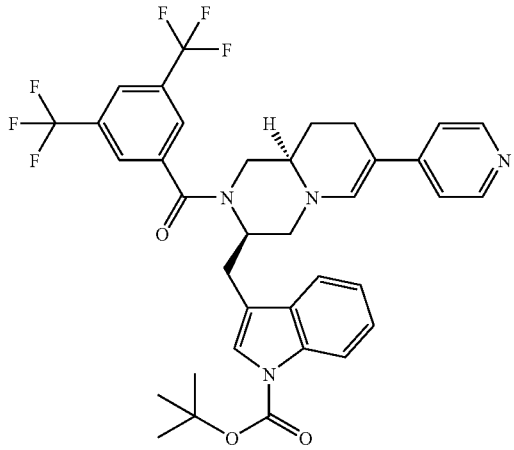

To mixture of (3R,9aR)-3-[2-(3,5-bis(trifluoromethyl)benzoyl)-7-trifluoromethanesulfonyloxy-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-trifluoromethanesulfonyloxy-1,3,4,8,9,9a-hexahydro-2H-pyrido[1,2-a]pyrazin-3-yl-methyl]-indole-1-carboxylic acid tert-butyl ester (0.9 g) in degassed 1,4-dioxane (40 ml) was added 4-tributylstannanylpyridine (0.67 g), lithium chloride (153 mg) and tetrakis(triphenylphosphine) palladium(0) (70 mg). The resulting mixture was heated at 80° C. for 20 hours. Subsequently the solvent was removed in vacuo, the residue dissolved in ethyl acetate, washed with a potassium fluoride solution, dried, filtered and concentrated in vacuo. The residue was purified by column chromatography (SiO$_2$, diethylether) to afford a mixture of (3R,9aR)-3-[2-(3,5-bis(trifluoromethyl)-benzoyl)-7-pyridin-4-yl-1,3,4,6,9,9a-hexahydro-2H-pyrido[1,2-a]pyrazin-3-ylmethyl]-indole-1-carboxylic acid tert-butyl ester and (3R,9aR)-3-[2-(3,5-bis(trifluoromethyl)-benzoyl)-7-pyridin-4-yl-1,3,4,8,9,9a-hexahydro-2H-pyrido[1,2-a]pyrazin-3-ylmethyl]-indole-1-carboxylic acid tert-butyl ester (0.25 g). $R_f$ 0.57 (SiO$_2$, diethylether).

In a similar way mixtures were prepared of:
(3R,9aR)-3-[2-(3,5-bis(trifluoromethyl)-benzoyl)-7-pyridin-3-yl-1,3,4,6,9,9a-hexahydro-2H-pyrido[1,2-a]pyrazin-3-ylmethyl]-indole-1-carboxylic acid tert-butyl ester and (3R,9aR)-3-[2-(3,5-bis(trifluoromethyl)-benzoyl)-7-pyridin-3-yl-1,3,4,8,9,9a-hexahydro-2H-pyrido[1,2-a]pyrazin-3-ylmethyl]-indole-1-carboxylic acid tert-butyl ester. $R_f$ 0.06 (SiO$_2$, diethylether).

(3R,9aR)-3-[2-(3,5-bis(trifluoromethyl)-benzoyl)-7-pyridin-2-yl-1,3,4,6,9,9a-hexahydro-2H-pyrido[1,2-a]pyrazin-3-ylmethyl]-indole-1-carboxylic acid tert-butyl ester and (3R,9aR)-3-[2-(3,5-bis(trifluoromethyl)-benzoyl)-7-pyridin-2-yl-1,3,4,8,9,9a-hexahydro-2H-pyrido[1,2-a]pyrazin-3-ylmethyl]-indole-1-carboxylic acid tert-butyl ester. $R_f$ 0.39 (SiO$_2$, diethylether).

(3R,9aR)-3-[2-(3,5-bis(trifluoromethyl)-benzoyl)-7-pyrimidin-5-yl-1,3,4,6,9,9a-hexahydro-2H-pyrido[1,2-a]pyrazin-3-ylmethyl]-indole-1-carboxylic acid tert-butyl ester and (3R,9aR)-3-[2-(3,5-bis(trifluoromethyl)-benzoyl)-7-pyrimidin-5-yl-1,3,4,8,9,9a-hexahydro-2H-pyrido[1,2-a]pyrazin-3-ylmethyl]-indole-1-carboxylic acid tert-butyl ester. $R_f$ 0.84 (SiO$_2$, CH$_2$Cl$_2$/MeOH/NH$_4$OH 93:7:0.5).

Example 11

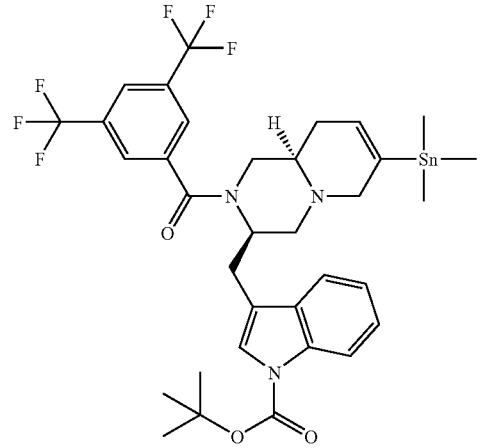

and

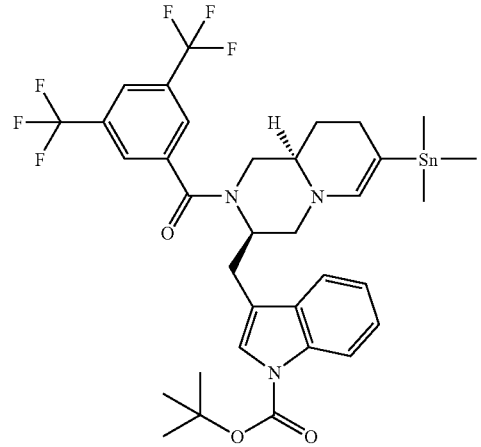

To mixture of (3R,9aR)-3-[2-(3,5-bis(trifluoromethyl)benzoyl)-7-trifluoromethane-sulfonyloxy-1,3,4,6,9,9a-hexahydro-2H-pyrido[1,2-a]pyrazin-3-yl-methyl]-indole-1- carboxylic acid tert-butyl ester and (3R,9aR)-3-[2-(3,5-bis(trifluoromethyl)-benzoyl)-7-trifluoromethanesulfonyloxy-1,3,4,8,9,9a-hexahydro-2H-pyrido[1,2-a]pyrazin-3-yl-methyl]-indole-1-carboxylic acid tert-butyl ester (0.76 g) in degassed tetrahydrofuran (40 ml) was added hexamethylditin (0.33 g), lithium chloride (0.26 g) and tetrakis(triphenylphosphine) palladium(0) (35 mg). The resulting mixture was heated at 65° C. for 3 hours, cooled to room temperature, and treated with a potassium fluoride solution. After addition of diethylether the layers were separated and the organic layer washed with an aqueous ammonium chloride solution, dried, filtered and concentrated in vacuo. The residue was purified by column chromatography (SiO$_2$, diethylether/hexanes 1:1) to afford a mixture of (3R,9aR)-3-[2-(3,5-bis(trifluoromethyl)benzoyl)-7-trimethylstannanyl-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-trimethylstannanyl-1,3,4,8,9,9a-hexahydro-2H-pyrido[1,2-a]pyrazin-3-yl-methyl]-indole-1-carboxylic acid tert-butyl ester (0.36 g). R$_f$ 0.49 (SiO$_2$, diethylether/hexanes 1:1).

Example 12

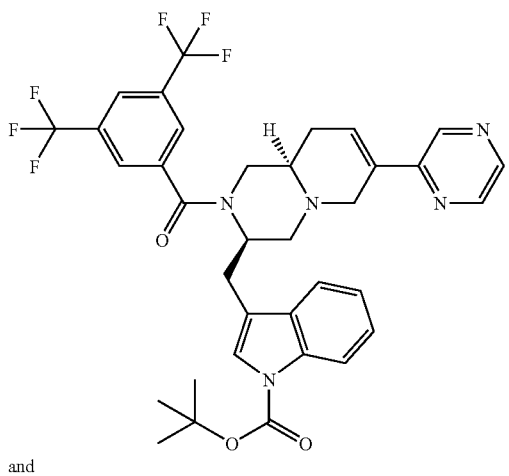

and

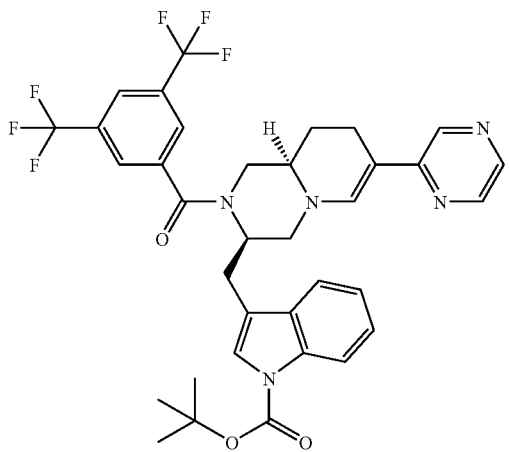

To a mixture of (3R,9aR)-3-[2-(3,5-bis(trifluoromethyl)benzoyl)-7-trimethylstannanyl-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-trimethylstannanyl-1,3,4,8,9,9a-hexahydro-2H-pyrido[1,2-a]pyrazin-3-yl-methyl]-indole-1-carboxylic acid tert-butyl ester (0.35 g) in degassed dimethylformamide (15 ml) was added 2-chloropyrazine (52 mg) and dichlorobis(triphenylphosphine)palladium(II) (24 mg). The resulting solution was stirred at 100° C. overnight, cooled to room temperature, diluted with diethylether and treated with a potassium fluoride solution. The layers were separated, the organic layer washed with water, dried, filtered and concentrated in vacuo. The residue was purified by column chromatography (SiO$_2$, diethylether) to afford a mixture of (3R,9aR)-3-[2-(3,5-bis(trifluoromethyl)benzoyl)-7-pyrazin-2-yl-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-pyrazin-2-yl-1,3,4,8,9,9a-hexahydro-2H-pyrido[1,2-a]pyrazin-3-yl-methyl]-indole-1-carboxylic acid tert-butyl ester (0.19 g). R$_f$ 0.30 (SiO$_2$, diethylether).

In a similar way a mixture of (3R,9aR)-3-[2-(3,5-bis(trifluoromethyl)benzoyl)-7-pyrimidin-2-yl-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-pyrimidin-2-yl-1,3,4,8,9,9a-hexahydro-2H-pyrido[1,2-a]pyrazin-3-yl-methyl]-indole-1-carboxylic acid tert-butyl ester was prepared. R$_f$ 0.54 (SiO$_2$, diethylether).

In a similar way a mixture of (3R,9aR)-3-[2-(3,5-bis(trifluoromethyl)benzoyl)-7-thiazol-2-yl-1,3,4,6,9,9a-hexahydro-2H-pyrido[1,2-a]pyrazin-3-yl-methyl]-indole-1-carboxylic acid tert-butyl ester and (3R,9aR)-3-[2-(3,5-bis(trifluoromethyl)-benzoyl)-7-thiazol-2-yl-1,3,4,8,9,9a, hexahydro-2H-pyrido[1,2-a]pyrazin-3-yl-methyl]-indole-1-carboxylic acid tert-butyl ester was prepared. R$_f$ 0.60 (SiO$_2$, diethylether).

Example 13

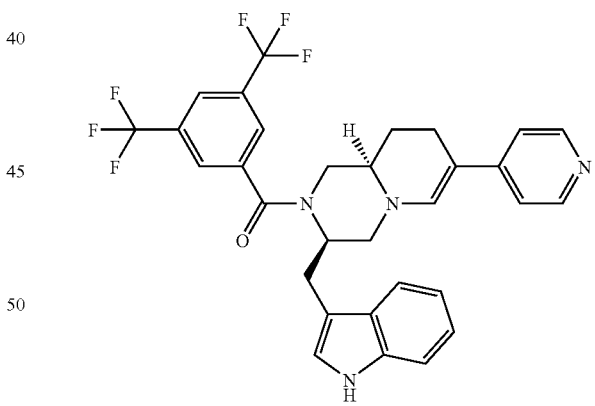

To mixture of anisole (35 mg), (3R,9aR)-3-[2-(3,5-bis(trifluoromethyl)-benzoyl)-7-pyridin-4-yl-1,3,4,6,9,9a-hexahydro-2H-pyrido[1,2-a]pyrazin-3-ylmethyl]-indole-1-carboxylic acid tert-butyl ester and (3R,9aR)-3-[2-(3,5-bis(trifluoromethyl)-benzoyl)-7-pyridin-4-yl-1,3,4,8,9,9a-hexahydro-2H-pyrido[1,2-a]pyrazin-3-ylmethyl]-indole-1-carboxylic acid tert-butyl ester (0.20 g) in dichloromethane (2 ml) was added trifluoroacetic acid, at 0° C. After 1.5 h at room temperature the mixture was diluted with dichloromethane, quenched with ice, and carefully basified with ammonium hydroxide. The layers were separated, the organic layer dried filtered and concentrated in vacuo. The residue was dissolved in methanol and heated at 50° C. for 1 h, then cooled to room temperature and concentrated in vacuo. The residual solid was stirred with hexanes overnight and then collected by filtration to afford (3R,9aR)-(3,5-bis(trifluoromethyl)phenyl)-[3-(1H-indol-3-ylmethyl)-7-pyridin-4-yl-1,3,4,8,9,9a-hexahydro-pyrido[1,2-a]pyrazin-2-yl]-methanone (compound 1) (70 mg). $R_f$ 0.51 (SiO$_2$, CH$_2$Cl$_2$/MeOH/NH$_4$OH 93:7:0.5).

In a similar way the following compounds were prepared:

(3R,9aR)-(3,5-bis(trifluoromethyl)phenyl)-[3-(1H-indol-3-ylmethyl)-7-pyridin-3-yl-1,3,4,8,9,9a-hexahydro-pyrido[1,2-a]pyrazin-2-yl]-methanone (compound 2). $R_f$ 0.74 (SiO$_2$, CH$_2$Cl$_2$/MeOH/NH$_4$OH 93:7:0.5).

(3R,9aR)-(3,5-bis(trifluoromethyl)phenyl)-[3-(1H-indol-3-ylmethyl)-7-pyridin-2-yl-1,3,4,8,9,9a-hexahydro-pyrido[1,2-a]pyrazin-2-yl]-methanone (compound 3). $R_f$ 0.60 (SiO$_2$, CH$_2$Cl$_2$/MeOH/NH$_4$OH 93:7:0.5).

(3R,9aR)-(3,5-bis(trifluoromethyl)phenyl)-[3-(1H-indol-3-ylmethyl)-7-pyrimidin-5-yl-1,3,4,8,9,9a-hexahydro-pyrido[1,2-a]pyrazin-2-yl]-methanone (compound 4). $R_f$ 0.62 (SiO$_2$, CH$_2$Cl$_2$/MeOH/NH$_4$OH 93:7:0.5).

(3R,9aR)-(3,5-bis(trifluoromethyl)phenyl)-[3-(1H-indol-3-ylmethyl)-7-pyrazin-2-yl-1,3,4,8,9,9a-hexahydro-pyrido[1,2-a]pyrazin-2-yl]-methanone (compound 5). $R_f$ 0.49 (SiO$_2$, CH$_2$Cl$_2$/MeOH/NH$_4$OH 93:7:0.5).

(3R,9aR)-(3,5-bis(trifluoromethyl)phenyl)-[3-(1H-indol-3-ylmethyl)-7-pyrimidin-2-yl-1,3,4,8,9,9a-hexahydro-pyrido[1,2-a]pyrazin-2-yl]-methanone (compound 6). $R_f$ 0.85 (SiO$_2$, CH$_2$Cl$_2$/MeOH/NH$_4$OH 85:15:1).

(3R,9aR)-(3,5-bis(trifluoromethyl)phenyl)-[3-(1H-indol-3-ylmethyl)-7-thiazol-2-yl-1,3,4,8,9,9a-hexahydro-pyrido[1,2-a]pyrazin-2-yl]-methanone (compound 7). $R_f$ 0.85 (SiO$_2$, CH$_2$Cl$_2$/MeOH/NH$_4$OH 85:15:1).

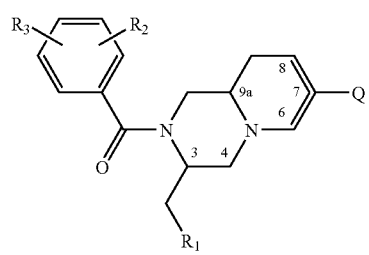

(1)

| | Substitution pattern | | | bonds | | Stereochem. | | |
|---|---|---|---|---|---|---|---|---|
| N | $R_1$ | $R_2$ | $R_3$ | Q | 6-7 | 7-8 | 3 | 7 | 9a |
| 1 | 3-indolyl | 3-CF$_3$ | 3-CF$_3$ | 4-pyridyl | d | s | R | — | R |
| 2 | 3-indolyl | 3-CF$_3$ | 3-CF$_3$ | 3-pyridyl | d | s | R | — | R |
| 3 | 3-indolyl | 3-CF$_3$ | 3-CF$_3$ | 2-pyridyl | d | s | R | — | R |
| 4 | 3-indolyl | 3-CF$_3$ | 3-CF$_3$ | 5-pyrimidyl | d | s | R | — | R |
| 5 | 3-indolyl | 3-CF$_3$ | 3-CF$_3$ | 2-pyrazinyl | d | s | R | — | R |
| 6 | 3-indolyl | 3-CF$_3$ | 3-CF$_3$ | 2-pyrimidyl | d | s | R | — | R |
| 7 | 3-indolyl | 3-CF$_3$ | 3-CF$_3$ | 2-thiazolyl | d | s | R | — | R | s = single bond,
d = double bond

EXAMPLE OF FORMULATION OF COMPOUNDS AS USED IN ANIMAL STUDIES

Formulation of Example 3

For oral (p.o.) administration: to the desired quantity (0.5-15 mg) of the solid Example 2 in a glass tube, some glass beads were added and the solid was milled by vortexing for 2 minutes. After addition of 1 ml of a solution of 1% methylcellulose in water, the compound was suspended by vortexing for 10 minutes. The pH was adjusted to 7 with a few drops of NaOH (0.1N in water). Remaining particles in the suspension were further suspended by using an ultrasonic bath.

| | PHARMACOLOGICAL DATA | |
|---|---|---|
| Comp. | affinity NK-1 binding pK$_i$ | In vivo antagonism Gerbil foot tapping p.o. ED$_{50}$ mg/kg |
| 1 | 7.8 | 1.7 |
| 2 | 7.7 | |
| 3 | 8.5 | 2.2 |
| 4 | 8.1 | |
| 5 | 8.6 | |
| 6 | 8.8 | |
| 7 | 9.2 | 3.4 |

What is claimed is:

1. A compound of formula (1):

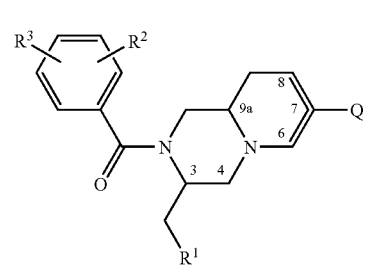

wherein:
   $R^1$ is a group chosen from phenyl, 2-indolyl, 3-indolyl, 3-indazolyl, and benzo[b]thiophen-3-yl, wherein the group is optionally substituted with a halogen or $C_1$-$C_3$ alkyl;
   $R^2$ and $R^3$, which may be the same or different, are chosen from a halogen, hydrogen, OCH$_3$, CH$_3$ and CF$_3$;
   Q is chosen from optionally substituted, aromatic or heteroaromatic five- or six-membered rings, connected by a carbon-carbon bond;
   the pyrido[1,2-a]pyrazine moiety optionally contains a double bond, wherein the double bond is between carbon atoms 6 and 7 or between carbon atoms 7 and 8; or
   at least one stereoisomer or pharmacologically acceptable salt thereof.

2. The compound of claim 1, wherein Q is an optionally substituted, six-membered, nitrogen containing heteroaromatic ring.

3. The compound of claim 1, wherein $R^1$ is 3-indolyl, $R^2$ and $R^3$ are CF$_3$ groups in the 3- and 5-positions, and Q is an optionally substituted, six-membered, nitrogen containing heteroaromatic ring.

4. The compound of claim 1, wherein said compound of formula (1) is chosen from:
   (3R, 9aR)-3,5-bis(trifluoromethyl)phenyl)-[3-(1H-indol-3-ylmethyl)-7-pyridin-4-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-3-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-5-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrazin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-thiazol-2-yl-1,3,4,8,9,9a-hexahydro-pyrido[1,2-a]pyrazin-2-yl]-methanone; and stereoisomers or pharmacologically acceptable salts thereof.

5. A pharmaceutical composition, comprising a pharmacologically active amount of at least one compound of formula (1):

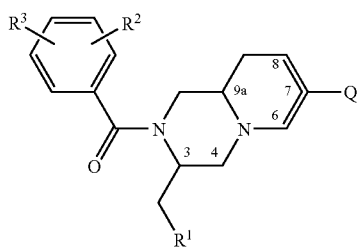

(1)

wherein:
R$^1$ is a group chosen from phenyl, 2-indolyl, 3-indolyl, 3-indazolyl, and benzo[b]thiophen-3-yl, wherein the group is optionally substituted with a halogen or C$_1$-C$_3$ alkyl;
R$^2$ and R$^3$, which may be the same or different, are chosen from a halogen, hydrogen, OCH$_3$, CH$_3$ and CF$_3$;
Q is chosen from optionally substituted, aromatic or heteroaromatic five- or six-membered rings, connected by a carbon-carbon bond;
the pyrido[1,2-a]pyrazine moiety optionally contains a double bond, wherein the double bond is between carbon atoms 6 and 7 or between carbon atoms 7 and 8; or
at least one stereoisomer or pharmacologically acceptable salt thereof.

6. The pharmaceutical composition of claim 5, wherein said compound of the general formula 1 is chosen from:
(3R, 9aR)-3,5-bis(trifluoromethyl)phenyl)-[3-(1H-indol-3-ylmethyl)-7-pyridin-4-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-3-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-5-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrazin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-2-yl-1,3,4,8,9,9a-hexahydro-pyrido[1,2-a]pyrazin-2-yl]-methanone;

(3R,9aR)-3,5-bis(trifluoromethyl)phenyl)-[3-(1H-indol-3-ylmethyl)-7-thiazol-2-yl-1,3,4,8,9,9a-hexahydro-pyrido[1,2-a]pyrazin-2-yl]-methanone; and stereoisomers or pharmacologically acceptable salts thereof.

7. A method for the treatment of at least one disorder involving neurokinins interacting with NK$_1$ receptors in a patient in need thereof, comprising: administering an effective amount of a pharmaceutical composition, wherein said pharmaceutical composition comprises at least one compound of formula (1):

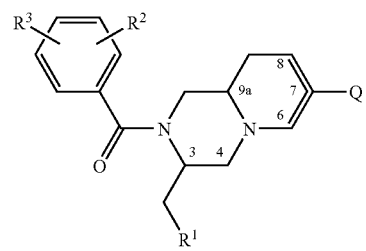

(1)

wherein:
R$^1$ is a group chosen from phenyl, 2-indolyl, 3-indolyl, 3-indazolyl, and benzo[b]thiophen-3-yl, wherein the group is optionally substituted with a halogen or C$_1$-C$_3$ alkyl;
R$^2$ and R$^3$, which may be the same or different, are chosen from a halogen, hydrogen, OCH$_3$, CH$_3$ and CF$_3$;
Q is chosen from optionally substituted, aromatic or heteroaromatic five- or six-membered rings, connected by a carbon-carbon bond;
the pyrido[1,2-a]pyrazine moiety optionally contains a double bond, wherein the double bond is between carbon atoms 6 and 7 or between carbon atoms 7 and 8; or
at least one stereoisomer or pharmacologically acceptable salt thereof, wherein the at least one disorder involving neurokinins interacting with NK$_1$ receptors is selected from the group consisting of acute and chronic pain, emesis, asthma, unipolar depressive disorders, minor depression, seasonal affective disorder, postnatal depression, dysthymia, major depression and anxiety.

8. The method of claim 7, wherein said compound of formula (1) is chosen from:
(3R, 9aR)-3,5-bis(trifluoromethyl)phenyl)-[3-(1H-indol-3-ylmethyl)-7-pyridin-4-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-3-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyridin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-5-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrazin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-pyrimidin-2-yl-1,3,4,8,9,9a-hexahydro-pyrido[1,2-a]pyrazin-2-yl]-methanone;

(3R, 9aR)-3,5-bis(trifluoromethyl)phenyl)-[3-(1H-indol-3-ylmethyl)-7-thiazol-2-yl-1,3,4,8,9,9a-hexahydro-pyrido[1,2-a]pyrazin-2-yl]-methanone; and stereoisomers or pharmacologically acceptable salts thereof.

* * * * *